(12) United States Patent
Kamali et al.

(10) Patent No.: US 8,414,921 B2
(45) Date of Patent: Apr. 9, 2013

(54) PHARMACEUTICAL COMPOSITIONS OF COMBINATIONS OF DIPEPTIDYL PEPTIDASE-4 INHIBITORS WITH METFORMIN

(75) Inventors: Ashkan Kamali, West Conshohocken, PA (US); Laman Alani, Lansdale, PA (US); Kyle A. Fliszar, Quakertown, PA (US); Soumojeet Ghosh, Lansdale, PA (US); Monica Tijerina, Doylestown, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/085,722

(22) PCT Filed: Dec. 12, 2006

(86) PCT No.: PCT/US2006/047380
§ 371 (c)(1),
(2), (4) Date: May 29, 2008

(87) PCT Pub. No.: WO2007/078726
PCT Pub. Date: Jul. 12, 2007

(65) Prior Publication Data
US 2009/0105265 A1  Apr. 23, 2009

Related U.S. Application Data

(60) Provisional application No. 60/750,954, filed on Dec. 16, 2005.

(51) Int. Cl.
*A61K 9/20* (2006.01)
(52) U.S. Cl. .................................................. 424/465
(58) Field of Classification Search .................. None
See application file for complete search history.

(56) References Cited

U.S. PATENT DOCUMENTS

| | | | |
|---|---|---|---|
| 6,548,481 B1 | 4/2003 | Demuth et al. | |
| 2003/0139434 A1 | 7/2003 | Balkan et al. | |
| 2003/0166578 A1 | 9/2003 | Arch et al. | |
| 2004/0229848 A1 | 11/2004 | Demuth et al. | |
| 2004/0254167 A1 | 12/2004 | Biftu et al. | |
| 2005/0051922 A1* | 3/2005 | Nangia et al. | 424/464 |
| 2006/0210627 A1 | 9/2006 | Pfeffer et al. | |
| 2006/0270701 A1* | 11/2006 | Kroth et al. | 514/300 |
| 2006/0270722 A1* | 11/2006 | Thornberry et al. | 514/374 |
| 2007/0072810 A1* | 3/2007 | Asakawa | 514/19 |
| 2007/0172525 A1 | 7/2007 | Sesha | |
| 2008/0064701 A1 | 3/2008 | Sesha | |
| 2009/0253752 A1* | 10/2009 | Burkey et al. | 514/342 |
| 2009/0304790 A1* | 12/2009 | Nilsson et al. | 424/464 |

FOREIGN PATENT DOCUMENTS

| | | |
|---|---|---|
| CA | 2 623 011 A1 | 4/2007 |
| EP | 1 557 165 A1 | 7/2005 |
| JP | 2003-520226 A | 7/2003 |
| JP | 2003-535898 A | 12/2003 |
| JP | 2005/041885 A | 2/2005 |
| JP | 2005-514377 A | 5/2005 |
| WO | 99/38501 A2 | 8/1999 |
| WO | 99/38501 A3 | 8/1999 |
| WO | 01/52825 A2 | 7/2001 |
| WO | 01/52825 A3 | 7/2001 |
| WO | 01/97808 A1 | 12/2001 |
| WO | WO 03/004498 A1 | 1/2003 |
| WO | 03/045977 A2 | 6/2003 |
| WO | 03/045977 A3 | 6/2003 |
| WO | 2004/028521 A1 | 4/2004 |
| WO | WO 2004/050022 A2 | 6/2004 |
| WO | WO 2004/050022 A3 | 6/2004 |
| WO | WO 2004/058266 A1 | 7/2004 |
| WO | WO 2005/013957 A2 | 2/2005 |
| WO | WO 2005/013957 A3 | 2/2005 |
| WO | 2005/041923 A1 | 5/2005 |
| WO | WO 2005/047297 A1 | 5/2005 |
| WO | 2005/082348 A2 | 9/2005 |
| WO | 2005/082849 A1 | 9/2005 |
| WO | WO 2006/047248 A1 | 5/2006 |
| WO | WO 2006/135723 A2 | 12/2006 |
| WO | WO 2006/135723 A3 | 12/2006 |
| WO | WO 2007/019255 A2 | 2/2007 |
| WO | WO 2007/019255 A3 | 2/2007 |
| WO | WO 2007/041053 A2 | 4/2007 |
| WO | WO 2007/041053 A3 | 4/2007 |

OTHER PUBLICATIONS

"Sitagliptin (MK-0431) for Type 2 Diabetes shows promise in Phase II clinical trials" from Medical News Today, Jun. 11, 2005, p. 1-3 (http://www.medicalnewstoday.com/releases/25962.php).*

Ahren, B., et al., "Improved Meal-Releated B-Cell Function and Insulin Sensitivity by the Dipeptidyl Peptidase-IV Inhibitor Vildagliptin in Metformin-Treated Patients With Type 2 Diabetes Over 1 Year", Diabetes Care, 2005, p. 1936-, vol. 28, No. 8.

Brazg, R. et al., "Effect of Adding MK-0431 to On-Going Motformin Therapy in Type 2 Diabetic Paitents Who Have Inadequate Glycemic Control on Metformin", Diabetes, 2005, p. A3, vol. 54, Suppl 1.

Goldstein, B. J. et al., "Effect of Initial Combination Therapy With Sitagliptin, a Dipeptidyl Peptidase-4 inhibitor, and Metformin on Glycomic Control in Patients With Type 2 Diabetes", Diabetes Care, 2007, p. 1979-, vol. 30, No. 8.

Herman, G. et al., "Co-Administration of MK-0431 and Metformin in Patients with Type 2 Diabetes Does Not Alter the Pharmacokinetics of MK-0431 or Metformin", p. A505.

* cited by examiner

*Primary Examiner* — Bethany Barham
(74) *Attorney, Agent, or Firm* — Baerbel R. Brown; John C. Todaro

(57) ABSTRACT

Disclosed are pharmaceutical compositions comprising fixed-dose combinations of a dipeptidyl peptidase-4 inhibitor and metformin, methods of preparing such pharmaceutical compositions, and methods of treating Type 2 diabetes with such pharmaceutical compositions.

28 Claims, No Drawings

PHARMACEUTICAL COMPOSITIONS OF COMBINATIONS OF DIPEPTIDYL PEPTIDASE-4 INHIBITORS WITH METFORMIN

CROSS REFERENCE TO RELATED APPLICATIONS

This application is the National Stage of International Application No. PCT/US2006/047380, filed 12 Dec. 2006, which claims the benefit under 35 U.S.C. 119(e) of U.S. Provisional Application No. 60/750,954, filed Dec. 16, 2005.

BACKGROUND OF THE INVENTION

Type 2 diabetes is a chronic and progressive disease arising from a complex pathophysiology involving the dual endocrine defects of insulin resistance and impaired insulin secretion. The treatment of Type 2 diabetes typically begins with diet and exercise, followed by oral antidiabetic monotherapy. For many patients, these regimens do not sufficiently control glycaemia during long-term treatment, leading to a requirement for combination therapy within several years following diagnosis. However, co-prescription of two or more oral antidiabetic drugs may result in treatment regimens that are complex and difficult for many patients to follow. Combining two or more oral antidiabetic agents into a single tablet provides a potential means of delivering combination therapy without adding to the complexity of patients' daily regimens. Such formulations have been well accepted in other disease indications, such as hypertension (HYZAAR™ which is a combination of losartan potassium and hydrochlorothiazide) and cholesterol lowering (VYTORIN™ which is a combination of simvastatin and ezetimibe). The selection of effective and well-tolerated treatments is a key step in the design of a combination tablet. Moreover, it is essential that the components have complementary mechanisms of action and compatible pharmacokinetic profiles. Examples of marketed combination tablets containing two oral antidiabetic agents include Glucovance™ (metformin and glyburide), Avandame™ (metformin and rosiglitazone), and Metaglip™ (metformin and glipizide).

Metformin represents the only oral antidiabetic agent proven to reduce the total burden of microvascular and macrovascular diabetic complications and to prolong the lives of Type 2 diabetic patients. Furthermore, metformin treatment is often associated with reductions in body weight in overweight patients and with improvements in lipid profiles in dyslipidemic patients.

Dipeptidyl peptidase-4 (DPP-4) inhibitors represent a novel class of agents that are being developed for the treatment or improvement in glycemic control in patients with Type 2 diabetes. Specific DPP-4 inhibitors currently in clinical trials for the treatment of Type 2 diabetes include sitagliptin phosphate (MK-0431), vildagliptin (LAF-237), saxagliptin (BMS47718), P93/01 (Prosidion), SYR322 (Takeda), GSK 823093, Roche 0730699, TS021 (Taisho), E3024 (Eisai), and PHX-1149 (Phenomix). For example, oral administration of vildagliptin or sitagliptin to human Type 2 diabetics has been found to reduce fasting glucose and postprandial glucose excursion in association with significantly reduced $HbA_{1c}$ levels. For reviews on the application of DPP-4 inhibitors for the treatment of Type 2 diabetes, reference is made to the following publications: (1) H.-U. Demuth, et al., "Type 2 diabetes—Therapy with dipeptidyl peptidase IV inhibitors," *Biochim. Biophys. Acta,* 1751: 33-44 (2005) and (2) K. Augustyns, et al., "Inhibitors of proline-specific dipeptidyl peptidases: DPP IV inhibitors as a novel approach for the treatment of Type 2 diabetes," *Expert Opin. Ther. Patents,* 15: 1387-1407 (2005).

Sitagliptin phosphate having structural formula I below is the dihydrogenphosphate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine.

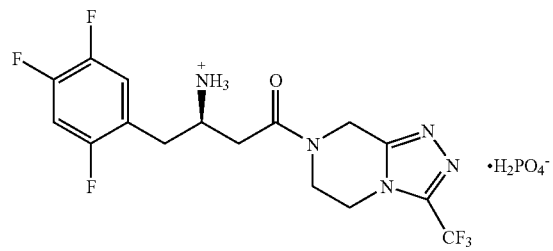

(I)

In one embodiment sitagliptin phosphate is in the form of a crystalline anhydrate or monohydrate. In a class of this embodiment, sitagliptin phosphate is in the form of a crystalline monohydrate. Sitagliptin free base and pharmaceutically acceptable salts thereof are disclosed in U.S. Pat. No. 6,699,871, the contents of which are hereby incorporated by reference in their entirety. Crystalline sitagliptin phosphate monohydrate is disclosed in international patent publication WO 2005/0031335 published on Jan. 13, 2005. For a review on sitagliptin phosphate (MK-0431) including its synthesis and pharmacological properties, reference is made to the following publications: (1) C. F. Deacon, "MK-431," *Curr. Opin. Invest. Drugs,* 6: 419-426 (2005) and (2) "MK-0431", *Drugs of the Future,* 30: 337-343 (2005).

Vildagliptin (LAF-237) is the generic name for (S)-1-[(3-hydroxy-1-adamantyl)amino]acetyl-2-cyano-pyrrolidine having structural formula II. Vildagliptin is specifically disclosed in U.S. Pat. No. 6,166,063, the contents of which are hereby incorporated by reference in their entirety.

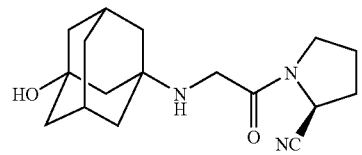

(II)

Saxagliptin (BMS-47718) is a methanoprolinenitrile of structural formula III below. Saxagliptin is specifically disclosed in U.S. Pat. No. 6,395,767, the contents of which are hereby incorporated by reference in their entirety.

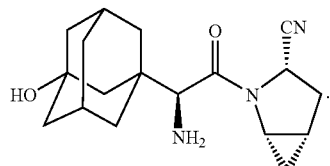

(III)

The present invention provides for pharmaceutical compositions of a fixed-dose combination of a DPP-4 inhibitor and metformin which are prepared by dry or wet processing methods. The pharmaceutical compositions of the present invention provide for immediate release of the two active pharmaceutical ingredients. In one embodiment the pharmaceutical compositions of the present invention are in the dosage form of a tablet, and, in particular, a film-coated tablet.

The present invention also provides a process to prepare pharmaceutical compositions of a fixed-dose combination of a DPP-4 inhibitor and metformin by dry or wet processing methods. The dry processing methods include dry compression and dry granulation, and the wet processing methods include wet granulation.

Another aspect of the present invention provides methods for the treatment of Type 2 diabetes by administering to a host in need of such treatment a therapeutically effective amount of a pharmaceutical composition of the present invention.

These and other aspects will become readily apparent from the detailed description which follows.

SUMMARY OF THE INVENTION

The present invention is directed to novel pharmaceutical compositions comprising fixed dose combinations of a DPP-4 inhibitor and metformin, or pharmaceutically acceptable salts of each thereof, methods of preparing such pharmaceutical compositions, and methods of treating Type 2 diabetes with such pharmaceutical compositions. In particular, the invention is directed to pharmaceutical compositions comprising fixed-dose combinations of sitagliptin phosphate and metformin hydrochloride.

DETAILED DESCRIPTION OF THE INVENTION

One aspect of the present invention is directed to dosage forms for the medicinal administration of a fixed-dose combination of a DPP-4 inhibitor and metformin. Such dosage forms may be in the powder or solid format and include tablets, capsules, sachets, etc. A particular solid dosage form relates to tablets comprising a fixed-dose combination of a DPP-4 inhibitor and metformin hydrochloride (1,1-dimethylbiguanide hydrochloride).

In a particular aspect of the present invention, the pharmaceutical compositions comprise (1) a DPP-4 inhibitor, or a pharmaceutically acceptable salt thereof, as one of the two active pharmaceutical ingredients; (2) metformin hydrochloride as the second active pharmaceutical ingredient; and (3) a lubricant or glidant. In an embodiment of this aspect of the present invention, the pharmaceutical compositions may also contain one or more excipients which excipients are selected from the group consisting of one or more binding agents (binders); one or more diluents; one or more surfactants or wetting agents; one or more disintegrants; and one or more antioxidants.

In another embodiment of this aspect of the invention, the DPP-4 inhibitor is selected from the group consisting of sitagliptin, vildagliptin, saxagliptin, P93/01, SYR322, GSK 823093, Roche 0730699, TS021, E3024, and PHX-1149. In a class of this embodiment the DPP-4 inhibitor is sitagliptin, vildagliptin, or saxagliptin. In a subclass of this class, the DPP-4 inhibitor is sitagliptin.

A preferred pharmaceutically acceptable salt of sitagliptin is the dihydrogenphosphate salt of structural formula I above (sitagliptin phosphate). A preferred form of the dihydrogenphosphate salt is the crystalline monohydrate disclosed in WO 2005/0031335.

The preparation of sitagliptin and pharmaceutically acceptable salts thereof is disclosed in U.S. Pat. No. 6,699, 871, the contents of which are herein incorporated by reference in their entirety. The preparation of sitagliptin phosphate monohydrate is disclosed in international patent publication WO 2005/0031335 published on Jan. 13, 2005, the contents of which are herein incorporated by reference in their entirety.

The dosage strength of the DPP-4 inhibitor for incorporation into the pharmaceutical compositions of the present invention is an amount from about 1 milligram to about 250 milligrams of the active moiety. A preferred dosage strength of the DPP-4 inhibitor is an amount from about 25 milligrams to about 200 milligrams of the active moiety. Discrete dosage strengths are the equivalent of 25, 50, 75, 100, 150, and 200 milligrams of the DPP-4 inhibitor active moiety. By "active moiety" is meant the free base form of the DPP-4 inhibitor as an anhydrate.

The unit dosage strength of sitagliptin free base anhydrate (active moiety) for inclusion into the fixed-dose combination pharmaceutical compositions of the present invention is 25, 50, 75, 100, 150, or 200 milligrams. A preferred dosage strength of sitagliptin is 50 or 100 milligrams. An equivalent amount of sitagliptin phosphate monohydrate to the sitagliptin free base anhydrate is used in the pharmaceutical compositions, namely, 32.13, 64.25, 96.38, 128.5, 192.75, and 257 milligrams, respectively.

The unit dosage strength of the metformin hydrochloride for incorporation into the fixed-dose combination of the present invention is 250, 500, 625, 750, 850, and 1000 milligrams. These unit dosage strengths of metformin hydrochloride represent the dosage strengths approved in the U.S. for marketing to treat Type 2 diabetes.

Specific embodiments of dosage strengths for sitagliptin and metformin hydrochloride in the fixed-dose combinations of the present invention are the following:
(1) 50 milligrams of sitagliptin (equivalent to 64.25 milligrams of sitagliptin phosphate monohydrate) and 500 milligrams metformin hydrochloride;
(2) 50 milligrams of sitagliptin (equivalent to 64.25 milligrams of sitagliptin phosphate monohydrate) and 850 milligrams metformin hydrochloride;
(3) 50 milligrams of sitagliptin (equivalent to 64.25 milligrams of sitagliptin phosphate monohydrate) and 1000 milligrams metformin hydrochloride;
(4) 100 milligrams of sitagliptin (equivalent to 128.5 milligrams of sitagliptin phosphate monohydrate) and 500 milligrams metformin hydrochloride;
(5) 100 milligrams of sitagliptin (equivalent to 128.5 milligrams of sitagliptin phosphate monohydrate) and 850 milligrams metformin hydrochloride; and
(6) 100 milligrams of sitagliptin (equivalent to 128.5 milligrams of sitagliptin phosphate monohydrate) and 1000 milligrams metformin hydrochloride.

The pharmaceutical compositions of the present invention are prepared by wet or dry processing methods. In one embodiment the pharmaceutical compositions are prepared by wet processing methods. In a class of this embodiment the pharmaceutical compositions are prepared by wet granulation methods. With wet granulation either high-shear granulation or fluid-bed granulation may be used. In one embodiment fluid-bed granulation is employed which has the advantage of affording tablets with higher diametric strength.

In a second embodiment the pharmaceutical compositions are prepared by dry processing methods. In a class of this embodiment the pharmaceutical compositions are prepared by direct compression or dry granulation methods. An embodiment of dry granulation is roller compaction.

The pharmaceutical compositions obtained by the dry or wet processing methods may be compressed into tablets, encapsulated, or metered into sachets.

The pharmaceutical compositions contain one or more lubricants or glidants. Examples of lubricants include magnesium stearate, calcium stearate, stearic acid, sodium stearyl fumarate, hydrogenated castor oil, and mixtures thereof. A preferred lubricant is magnesium stearate or sodium stearyl fumarate or a mixture thereof. Examples of glidants include colloidal silicon dioxide, calcium phosphate tribasic, magnesium silicate, and talc.

The pharmaceutical compositions of the present invention optionally contain one or more binding agents. Embodiments of binding agents include hydroxypropylcellulose (HPC), hydroxypropylmethyl cellulose (HMPC), hydroxyethyl cellulose, starch 1500, polyvinylpyrrolidone (povidone), and co-povidone. A preferred binding agent is polyvinylpyrrolidone.

The pharmaceutical compositions of the present invention may also optionally contain one or more diluents. Examples of diluents include mannitol, sorbitol, dibasic calcium phosphate dihydrate, microcrystalline cellulose, and powdered cellulose. A preferred diluent is microcrystalline cellulose. Microcrystalline cellulose is available from several suppliers and includes Avicel PH 101, Avicel PH 102, Avicel, PH 103, Avicel PH 105, and Avicel PH 200, manufactured by the FMC Corporation.

The pharmaceutical compositions of the present invention may also optionally contain a disintegrant. The disintegrant may be one of several modified starches, modified cellulose polymers, or polycarboxylic acids, such as croscarmellose sodium, sodium starch glycollate, polacrilin potassium, and carboxymethylcellulose calcium (CMC Calcium). In one embodiment, the disintegrant is croscarmellose sodium. Croscarmellose sodium NF Type A is commercially available under the trade name "Ac-di-sol."

The pharmaceutical compositions of the present invention may also optionally contain one or more surfactants or wetting agents. The surfactant may be anionic, cationic, or neutral. Anionic surfactants include sodium lauryl sulfate, sodium dodecanesulfonate, sodium oleyl sulfate, and sodium laurate mixed with stearates and talc. Cationic surfactants include benzalkonium chlorides and alkyltrimethylammonium bromides. Neutral surfactants include glyceryl monooleate, polyoxyethylene sorbitan fatty acid esters, polyvinyl alcohol, and sorbitan esters. Embodiments of wetting agents include poloxamer, polyoxyethylene alkyl ethers, polyoxyethylene castor oil derivatives, and polyoxyethylene stearates.

An anti-oxidant may optionally be added to the formulation to impart chemical stability. The anti-oxidant is selected from the group consisting of α-tocopherol, γ-tocopherol, δ-tocopherol, extracts of natural origin rich in tocopherol, L-ascorbic acid and its sodium or calcium salts, ascorbyl palmitate, propyl gallate, octyl gallate, dodecyl gallate, butylated hydroxytoluene (BHT), and butylated hydroxyanisole (BHA). In one embodiment, the antioxidant is BHT or BHA.

Preferred dosage forms for the pharmaceutical compositions of the present invention are tablets which are prepared by compression methods. Such tablets may be film-coated such as with a mixture of hydroxypropylcellulose and hydroxypropylmethylcellulose containing titanium dioxide and/or other coloring agents, such as iron oxides, dyes, and lakes; a mixture of polyvinyl alcohol (PVA) and polyethylene glycol (PEG) containing titanium dioxide and/or other coloring agents, such as iron oxides, dyes, and lakes; or any other suitable immediate-release film-coating agent(s). The coat provides taste masking and additional stability to the final tablet. A commercial film-coat is Opadry® which is a formulated powder blend provided by Colorcon.

Finally, a sweetening agent and/or flavoring agent may be added if desired.

In one embodiment of the present invention, the pharmaceutical compositions contain about 3 to 20% by weight of a DPP-4 inhibitor as one of the two pharmaceutically active ingredients; about 25 to 94% by weight of metformin hydrochloride as the second pharmaceutically active ingredient; about 0 to 35% by weight of a binding agent; and about 0.1 to 10% by weight of a lubricant. In a class of this embodiment the binding agent is polyvinylpyrrolidone or hydroxypropylcellulose, and the lubricant is magnesium stearate or sodium stearyl fumarate. In a subclass of this class, the binding agent is polyvinylpyrrolidone, and the lubricant is sodium stearyl fumarate. In another class the pharmaceutical compositions optionally contain about 0 to 3% by weight of a surfactant and/or about 0 to 70% by weight of a diluent. In a subclass of this class, the surfactant is sodium lauryl sulfate and the diluent is microcrystalline cellulose.

In a second embodiment the pharmaceutical compositions of the present invention are prepared by wet granulation methods and comprise about 5 to 18% by weight of a DPP-4 inhibitor as one of the two pharmaceutically active ingredients; about 65 to 77% by weight of metformin hydrochloride as the second pharmaceutically active ingredient; about 4 to 9% by weight of a binding agent; and about 1 to 2% by weight of a lubricant. In a class of this embodiment the binding agent is polyvinylpyrrolidone or hydroxypropylcellulose, and the lubricant is magnesium stearate or sodium stearyl fumarate. In a subclass of this class, the binding agent is polyvinylpyrrolidone. In another class the pharmaceutical compositions optionally contain about 0.5 to 1% to by weight of a surfactant and/or about 5 to 15% by weight of a diluent. In a subclass of this class, the surfactant is sodium lauryl sulfate and the diluent is microcrystalline cellulose.

In a further embodiment of the present invention, the pharmaceutical compositions as envisioned for commercial development are as follows:

Tablets of 50 mg DPP-4 Inhibitor/500 mg Metformin HCl Potency:

About 9% by weight of the DPP-4 inhibitor; about 73% by weight of metformin hydrochloride; about 7% by weight of a binding agent; about 1 to 2% by weight of a lubricant; and optionally about 10% by weight of a diluent and/or about 0.5% by weight of a surfactant. In a class of this embodiment the DPP-4 inhibitor is sitagliptin, vildagliptin, or saxagliptin; the binding agent is polyvinylpyrrolidone, the lubricant is magnesium stearate or sodium stearyl fumarate, the diluent is microcrystalline cellulose, and the surfactant is sodium lauryl sulfate. In a subclass of this class, the DPP-4 inhibitor is sitagliptin.

Tablets of 50 mg DPP-4 Inhibitor/850 mg Metformin HCl Potency:

About 6% by weight of the DPP-4 inhibitor; about 76% by weight of metformin hydrochloride; about 7% by weight of a binding agent; about 1 to 2% by weight of a lubricant; and optionally about 10% by weight of a diluent and/or about 0.5% by weight of a surfactant. In a class of this embodiment the DPP-4 inhibitor is sitagliptin, vildagliptin, or saxagliptin; the binding agent is polyvinylpyrrolidone, the lubricant is magnesium stearate or sodium stearyl fumarate, the diluent is microcrystalline cellulose, and the surfactant is sodium lauryl sulfate. In a subclass the DPP-4 inhibitor is sitagliptin.

Tablets of 50 mg DPP-4 Inhibitor/1000 mg Metformin HCl Potency:

About 5% by weight of the DPP-4 inhibitor; about 77% by weight of metformin hydrochloride; about 7% by weight of a binding agent; about 1 to 2% by weight of a lubricant; and optionally about 10% by weight of a diluent and/or about 0.5% by weight of a surfactant. In a class of this embodiment the DPP-4 inhibitor is sitagliptin, vildagliptin, or saxagliptin; the binding agent is polyvinylpyrrolidone, the lubricant is magnesium stearate or sodium stearyl fumarate, the diluent is microcrystalline cellulose, and the surfactant is sodium lauryl sulfate. In a subclass the DPP-4 inhibitor is sitagliptin.

Tablets of 100 mg DPP-4 Inhibitor/500 mg Metformin HCl Potency:

About 17% by weight of the DPP-4 inhibitor; about 65% by weight of metformin hydrochloride; about 7% by weight of a binding agent; about 1 to 2% by weight of a lubricant; and optionally about 9% by weight of a diluent and/or about 0.5% by weight of a surfactant. In a class of this embodiment the DPP-4 inhibitor is sitagliptin, vildagliptin, or saxagliptin; the binding agent is polyvinylpyrrolidone, the lubricant is magnesium stearate or sodium stearyl fumarate, the diluent is microcrystalline cellulose, and the surfactant is sodium lauryl sulfate. In a subclass the DPP-4 inhibitor is sitagliptin.

Tablets of 100 mg DPP-4 Inhibitor/850 mg Metformin HCl Potency:

About 11% by weight of the DPP-4 inhibitor; about 75% by weight of metformin hydrochloride; about 7% by weight of a binding agent; about 1 to 2% by weight of a lubricant; and optionally about 4% by weight of a diluent and/or about 0.5% by weight of a surfactant. In a class of this embodiment the DPP-4 inhibitor is sitagliptin, vildagliptin, or saxagliptin; the binding agent is polyvinylpyrrolidone, the lubricant is magnesium stearate or sodium stearyl fumarate, the diluent is microcrystalline cellulose, and the surfactant is sodium lauryl sulfate. In a subclass the DPP-4 inhibitor is sitagliptin.

Tablets of 100 mg DPP-4 Inhibitor/1000 mg Metformin HCl Potency:

About 10% by weight of the DPP-4 inhibitor; about 77% by weight of metformin hydrochloride; about 7% by weight of a binding agent; about 1 to 2% by weight of a lubricant; and optionally about 4% by weight of a diluent and/or about 0.5% by weight of a surfactant. In a class of this embodiment the DPP-4 inhibitor is sitagliptin, vildagliptin, or saxagliptin; the binding agent is polyvinylpyrrolidone, the lubricant is magnesium stearate or sodium stearyl fumarate, the diluent is microcrystalline cellulose, and the surfactant is sodium lauryl sulfate. In a subclass the DPP-4 inhibitor is sitagliptin.

The pharmaceutical tablet compositions of the present invention may also contain one or more additional formulation ingredients selected from a wide variety of excipients known in the pharmaceutical formulation art. According to the desired properties of the pharmaceutical composition, any number of ingredients may be selected, alone or in combination, based upon their known uses in preparing tablet compositions. Such ingredients include, but are not limited to, diluents, compression aids, glidants, disintegrants, lubricants, flavors, flavor enhancers, sweeteners, and preservatives.

The term "tablet" as used herein is intended to encompass compressed pharmaceutical dosage formulations of all shapes and sizes, whether coated or uncoated. Substances which may be used for coating include hydroxypropylcellulose, hydroxypropylmethylcellulose, titanium dioxide, talc, sweeteners, colorants, and flavoring agents.

In one embodiment the pharmaceutical compositions of the present invention are prepared by wet granulation (high shear and/or fluid bed). Granulation is a process in which binding agent is added either through the granulating solution or through addition to the granulating bowl to form granules. The steps involved in the wet granulation method comprise the following:

(1) the active pharmaceutical ingredients metformin hydrochloride and the DPP-4 inhibitor are added to the granulating bowl;
(2) optional disintegrants are added to step 1;
(3) for high shear granulation, the binding agent (such as polyvinylpyrrolidone or hydroxypropylcellulose) is added dry to the granulating bowl and dry mixed for a short period followed by the addition of water with or without a surfactant (such as sodium lauryl sulfate). For fluid bed granulation, both active pharmaceutical ingredients are added to the granulator bowl and the granulating solution comprised of binding agent with or without surfactant in water is added upon fluidization;
(4) granules prepared by high shear granulation are tray-dried in an oven or dried in a fluid bed dryer. For granules prepared by fluid bed granulation, granules are dried in a fluid bed dryer;
(5) dried granules are resized in suitable mill;
(6) optional diluents (such as microcrystalline cellulose and dibasic calcium phosphate dihydrate) are blended with dried granules in a suitable blender;
(7) lubricants or glidants (such as magnesium stearate and sodium stearyl fumarate) are added to the blend from step 6 in a suitable blender;
(8) lubricated granule mixture from step 7 may be filled into bottles, sachets, or capsules or compressed into desired tablet image;
(9) and if desired, the resulting tablets may be film-coated.

The steps involved in the dry processing (direct compression or dry granulation) methods comprise:

(1) the active pharmaceutical ingredients metformin hydrochloride and the DPP-4 inhibitor are added to a suitable blender;
(2) optional disintegrants are added to step 1;
(3) optional binders and/or diluents are added to step 2;
(4) lubricants or glidants are added to step 3;
(5) mixture from step 4 may be filled into bottles, sachets, or capsules or compressed into desired tablet image, or processed through a roller compactor;
(6) if processed through a roller compaction, granules may be resized in a suitable mill, if necessary;
(7) optional diluents may be added to the resulting granules, in a suitable blender to improve compaction properties;
(8) optional lubricants or glidants are added to the blend from step 7;
(9) lubricated granule mixture from step 8 may be filled into bottles, sachets, or capsules or compressed into desired tablet image;
(10) and if desired, the resulting tablets from step 5 or step 9 may be film-coated.

The present invention also provides methods for treating Type 2 diabetes by orally administering to a host in need of such treatment a therapeutically effective amount of one of the fixed-dose combination pharmaceutical compositions of the present invention. In one embodiment the host in need of such treatment is a human. In another embodiment the pharmaceutical composition is in the dosage form of a tablet. The pharmaceutical compositions comprising the fixed-dose combination may be administered once-daily (QD), twice-daily (BID), or thrice-daily (TID).

The following examples further describe and demonstrate embodiments within the scope of the present invention. The examples are given solely for the purpose of illustration and are not intended to be construed as limitations of the present invention as many variations thereof are possible without departing from the spirit and scope of the invention.

EXAMPLE 1

Fixed-Dose Combination of 50 Milligrams Sitagliptin and 500 Milligrams Metformin Hydrochloride/Per Tablet—Wet Granulation

| | |
|---|---|
| Sitagliptin phosphate monohydrate | 64.25 mg* |
| Metformin hydrochloride | 500 mg |
| Polyvinylpyrrolidone | 48.2 mg |
| Sodium lauryl sulfate (SLS) | 3.45 mg |
| Microcrystalline cellulose (Avicel PH-102) | 59.3 mg |
| Sodium stearyl fumarate | 13.8 mg |
| Purified water for granulation step** | 39.8 mg for high shear or 354 mg for fluid bed |
| Opadry ® II | 17.2 mg |
| Purified water for coating step** | 68.9 mg |

*Equivalent to 50 mg of sitagliptin free base anhydrate.
**Removed during processing.

Method of Manufacture:

Sitagliptin phosphate monohydrate and metformin hydrochloride were loaded into a high shear granulator or a fluid bed granulator. In the case of high shear granulation, purified water containing sodium lauryl sulfate was added to the APIs, in addition to the polyvinylpyrrolidone binding agent over a period of 3-5 minutes. The wetted mass was either tray dried at 40° C. or dried in a fluid-bed dryer at an inlet temperature of 45-60° C. for 3-6 minutes. In the case of fluid bed granulation, purified water containing polyvinylpyrrolidone and sodium lauryl sulfate was added to APIs over a period of 30-60 minutes. The wetted mass was dried in a fluid-bed dryer at an inlet temperature of 45-60° C. The dried material was then milled using a co-mill to achieve fine granules. After milling, microcrystalline cellulose was added to the granules and blended in a twin shell-blender for 200 revolutions. The lubricant (sodium stearyl fumarate) was then added and blended an additional 100 revolutions. The lubricated mixture was compressed using a rotary tablet press to provide a 689 mg uncoated tablet. The tablets were optionally coated with Opadry® II suspension (polyvinyl alcohol, polyethylene glycol, titanium dioxide, and talc, with or without colorants) to an approximate 2.5% weight gain to provide a 706 mg coated tablet.

EXAMPLE 2

Fixed-Dose Combination of 50 Milligrams Sitagliptin and 850 Milligrams Metformin Hydrochloride/Per Tablet—Wet Granulation

| | |
|---|---|
| Sitagliptin phosphate monohydrate | 64.25 mg* |
| Metformin hydrochloride | 850 mg |
| Polyvinylpyrrolidone | 78.2 mg |
| Sodium lauryl sulfate (SLS) | 5.60 mg |
| Microcrystalline cellulose (Avicel PH-102) | 96.1 mg |
| Sodium stearyl fumarate | 22.3 mg |
| Purified water for granulation step** | 64.9 mg for high shear or 573 mg for fluid bed |
| Opadry ® II | 27.9 mg |
| Purified water for coating step** | 112 mg |

*Equivalent to 50 mg of sitagliptin free base anhydrate.
**Removed during processing.

Method of Manufacture:

Tablets were prepared by wet-granulation using essentially the procedure of Example 1 to provide a 1117 mg uncoated tablet. The tablets were optionally coated with 27.9 mg of a standard Opadry II® film-coat formula to provide a 1145 mg coated tablet.

EXAMPLE 3

Fixed-Dose Combination of 50 Milligrams Sitagliptin and 1000 Milligrams Metformin Hydrochloride/Per Tablet—Wet Granulation

| | |
|---|---|
| Sitagliptin phosphate monohydrate | 64.25 mg* |
| Metformin hydrochloride | 1000 mg |
| Polyvinylpyrrolidone | 91.0 mg |
| Sodium lauryl sulfate (SLS) | 6.50 mg |
| Microcrystalline cellulose (Avicel PH-102) | 112.3 mg |
| Sodium stearyl fumarate | 26 mg |
| Purified water for granulation step** | 75.5 mg for high shear or 667 mg for fluid bed |
| Opadry ® II | 32.5 mg |
| Purified water for coating step** | 130 mg |

*Equivalent to 50 mg of sitagliptin free base anhydrate.
**Removed during processing.

Method of Manufacture:

Tablets were prepared by wet-granulation using essentially the procedure of Example 1 to provide a 1300 mg uncoated tablet. The tablets were optionally coated with an Opadry® II suspension (polyvinyl alcohol, polyethylene glycol, titanium dioxide, and talc, with or without colorants) to an approximate 2.5% weight gain to provide a 1333 mg coated tablet.

EXAMPLE 4

Fixed-Dose Combination of 50 Milligrams Sitagliptin and 500 Milligrams Metformin Hydrochloride/Per Tablet—Wet Granulation

| | |
|---|---|
| Sitagliptin phosphate monohydrate | 64.25 mg* |
| Metformin hydrochloride | 500 mg |
| Polyvinylpyrrolidone | 48.2 mg |
| Microcrystalline cellulose (Avicel PH-102) | 69.6 mg |
| Magnesium stearate | 6.89 |
| Purified water for granulation step** | 39.8 mg for high shear or 354 mg for fluid bed |
| Opadry ® II | 17.2 mg |
| Purified water for coating step** | 68.9 mg |

*Equivalent to 50 mg of sitagliptin free base anhydrate.
**Removed during processing.

Method of Manufacture:

Sitagliptin phosphate monohydrate and metformin hydrochloride were loaded into a high shear granulator or a fluid bed granulator. In the case of high shear granulation, purified water was added to the APIs, in addition to the polyvinylpyrrolidone binding agent over a period of 3-5 minutes. The wetted mass was either tray dried at 40° C. or dried in a fluid-bed dryer at an inlet temperature of 45-60° C. for 3-6 minutes. In the case of fluid bed granulation, purified water containing polyvinylpyrrolidone was added to APIs over a period of 30-60 minutes. The wetted mass was dried in a fluid-bed dryer at an inlet temperature of 45-60° C. The dried material was then milled using a co-mill to achieve fine granules. After milling, microcrystalline cellulose was added to the granules and blended in a twin shell-blender for 200 revolutions. The lubricant (magnesium stearate) was then added and blended an additional 100 revolutions. The lubricated mixture was compressed using a rotary tablet press to provide a 689 mg uncoated tablet. The tablet was then optionally film-coated with an Opadry® II suspension (polyvinyl alcohol, polyethylene glycol, titanium dioxide, and talc, with or without colorants) to an approximate 2.5% weight gain to provide a 706 mg coated tablet.

EXAMPLE 5

Fixed-Dose Combination of 50 Milligrams Sitagliptin and 1000 Milligrams Metformin Hydrochloride/Ter Tablet—Wet Granulation

| | |
|---|---|
| Sitagliptin phosphate monohydrate | 64.25 mg* |
| Metformin hydrochloride | 1000 mg |
| Polyvinylpyrrolidone | 91.0 mg |
| Microcrystalline cellulose (Avicel PH-102) | 125.25 mg |
| Magnesium stearate | 13.0 |
| Sodium lauryl sulfate | 6.5 |
| Purified water for granulation step** | 75.5 mg for high shear or 667 mg for fluid bed |
| Opadry ® II | 32.5 mg |
| Purified water for coating step** | 130 mg |

*Equivalent to 50 mg of sitagliptin free base anhydrate.
**Removed during processing.

Method of Manufacture:

Sitagliptin phosphate monohydrate and metformin hydrochloride were loaded into a high shear granulator or a fluid bed granulator. In the case of high shear granulation, purified water containing sodium lauryl sulfate was added to the APIs, in addition to the polyvinylpyrrolidone binding agent over a period of 3-5 minutes. The wetted mass was either tray dried at 40° C. or dried in a fluid-bed dryer at an inlet temperature of 45-60° C. for 3-6 minutes. In the case of fluid bed granulation, purified water containing polyvinylpyrrolidone and sodium lauryl sulfate was added to APIs over a period of 30-60 minutes. The wetted mass was dried in a fluid-bed dryer at an inlet temperature of 45-60° C. The dried material was then milled using a co-mill to achieve fine granules. After milling, microcrystalline cellulose was added to the granules and blended in a twin shell-blender for 200 revolutions. The lubricant (magnesium stearate) was then added and blended an additional 100 revolutions. The lubricated mixture was compressed using a rotary tablet press to provide a 1300 mg uncoated tablet. The tablet was then optionally film-coated with an Opadry® II suspension (polyvinyl alcohol, polyethylene glycol, titanium dioxide, and talc, with or without colorants) to an approximate 2.5% weight gain to provide a 1333 mg coated tablet.

EXAMPLE 6

Fixed-Dose Combination of 100 Milligrams Sitagliptin and 1000 Milligrams Metformin Hydrochloride/Per Tablet—Wet Granulation

| | |
|---|---|
| Sitagliptin phosphate monohydrate | 128.5 mg* |
| Metformin hydrochloride | 1000 mg |
| Polyvinylpyrrolidone | 91.0 mg |
| Sodium lauryl sulfate (SLS) | 6.50 mg |
| Microcrystalline cellulose (Avicel PH-102) | 48 mg |
| Sodium stearyl fumarate | 26 mg |
| Purified water** | 667 mg |

*Equivalent to 100 mg of sitagliptin free base anhydrate.
**Removed during processing.

Method of Manufacture:

Tablets were prepared by fluid-bed granulation using essentially the procedure of Example 1 to provide a 1300 mg uncoated tablet.

EXAMPLE 7

Fixed-Dose Combination of 100 Milligrams Sitagliptin and 500 Milligrams Metformin Hydrochloride/Per Tablet—Wet Granulation

| | |
|---|---|
| Sitagliptin phosphate monohydrate | 128.5 mg* |
| Metformin hydrochloride | 500 mg |
| Polyvinylpyrrolidone | 53.8 mg |
| Sodium lauryl sulfate (SLS) | 3.84 mg |
| Microcrystalline cellulose (Avicel PH-102) | 66.5 mg |
| Sodium stearyl fumarate | 15.4 mg |
| Purified water** | 394 mg |

*Equivalent to 50 mg of sitagliptin free base anhydrate.
**Removed during processing.

Method of Manufacture:

Tablets were prepared by fluid-bed granulation using essentially the procedure of Example 1 to provide a 768 mg uncoated tablet.

What is claimed is:

1. A pharmaceutical composition comprising:
   (a) about 3 to 20% by weight of sitagliptin, or a pharmaceutically acceptable salt thereof;
   (b) about 25 to 94% by weight of metformin hydrochloride;
   (c) about 0.1 to 10% by weight of a lubricant;
   (d) about 0 to 35% by weight of a binding agent;
   (e) about 0.5 to 1% by weight of a surfactant; and
   (f) about 5 to 15% by weight of a diluent.

2. The pharmaceutical composition of claim 1 additionally comprising one or more excipients selected from the group consisting of (a) a disintegrant; (b) a wetting agent; and (c) an anti-oxidant.

3. The pharmaceutical composition of claim 1 comprising:
   (a) about 5 to 18% by weight of sitagliptin, or a pharmaceutically acceptable salt thereof;
   (b) about 65 to 77% by weight of metformin hydrochloride;

(c) about 1 to 2% by weight of a lubricant;
(d) about 4 to 9% by weight of a binding agent;
(e) about 0.5 to 1% by weight of a surfactant; and
(f) about 5 to 15% by weight of a diluent.

4. The pharmaceutical composition of claim 3 wherein said lubricant is magnesium stearate or sodium stearyl fumarate, and the binding agent is polyvinylpyrrolidone.

5. The pharmaceutical composition of claim 3 comprising:
   (a) about 9% by weight of sitagliptin, or a pharmaceutically acceptable salt thereof;
   (b) about 73% by weight of metformin hydrochloride;
   (c) about 1 to 2% by weight of a lubricant;
   (d) about 7% by weight of a binding agent;
   (e) about 0.5 to 1% by weight of a surfactant; and
   (f) about 5 to 15% by weight of a diluent.

6. The pharmaceutical composition of claim 5 additionally comprising about 0.5% by weight of a surfactant and about 10% by weight of a diluent.

7. The pharmaceutical composition of claim 3 comprising
   (a) about 5% by weight of sitagliptin, or a pharmaceutically acceptable salt thereof;
   (b) about 77% by weight of metformin hydrochloride;
   (c) about 1 to 2% by weight of a lubricant;
   (d) about 7% by weight of a binding agent;
   (e) about 0.5 to 1% by weight of a surfactant; and
   (f) about 5 to 15% by weight of a diluent.

8. The pharmaceutical composition of claim 7 additionally comprising about 0.5% by weight of a surfactant and about 10% by weight of a diluent.

9. The pharmaceutical composition of claim 1 wherein the salt is the dihydrogenphosphate salt.

10. A pharmaceutical composition comprising:
    (a) sitagliptin present in a unit dosage strength of 25 to 200 milligrams;
    (b) metformin hydrochloride present in a unit dosage strength of 250, 500, 625, 750, 850, or 1000 milligrams;
    (c) about 1 to 2% by weight of a lubricant;
    (d) about 7% by weight of a binding agent;
    (e) about 10% by weight of a diluent; and
    (f) about 0.5% by weight of a surfactant.

11. The pharmaceutical composition of claim 10 wherein said lubricant is sodium stearyl fumarate, said binding agent is polyvinylpyrrolidone, said diluent is microcrystalline cellulose, and said surfactant is sodium lauryl sulfate.

12. The pharmaceutical composition of claim 10 wherein sitagliptin is present in a unit dosage strength of 25, 50, 75, 100, 150, or 200 milligrams, and said metformin hydrochloride is present in a unit dosage strength of 500, 850, or 1000 milligrams.

13. The pharmaceutical composition of claim 12 wherein sitagliptin is present in a unit dosage strength of 50 milligrams, and said metformin hydrochloride is present in a unit dosage strength of 500, 850, or 1000 milligrams.

14. The pharmaceutical composition of claim 12 wherein said sitagliptin is present in a unit dosage strength of 50 milligrams, and said metformin hydrochloride is present in a unit dosage strength of 500 or 1000 milligrams.

15. The pharmaceutical composition of claim 1 wherein said composition is in the dosage form of a tablet.

16. A method of treating Type 2 diabetes in a human in need thereof comprising orally administering to said human a pharmaceutical composition of claim 1.

17. The pharmaceutical composition of claim 1 further comprising one or more agents selected from the group consisting of flavoring agents, colorants, and sweeteners.

18. The pharmaceutical composition of claim 1 prepared by wet granulation methods.

19. The pharmaceutical composition of claim 12 wherein said composition is in the dosage form of a tablet.

20. A method of treating Type 2 diabetes in a human in need thereof comprising orally administering to said human a pharmaceutical composition of claim 12.

21. A pharmaceutical composition consisting essentially of:
    (a) about 3 to 20% by weight of sitagliptin, or a pharmaceutically acceptable salt thereof;
    (b) about 25 to 94% by weight of metformin hydrochloride;
    (c) about 0.1 to 10% by weight of a lubricant;
    (d) about 0 to 35% by weight of a binding agent;
    (e) about 0.5 to 1% by weight of a surfactant; and
    (f) about 5 to 15% by weight of a diluent.

22. A pharmaceutical composition in the form of a tablet comprising:
    a) 64.25 mg[*] of sitagliptin phosphate monohydrate, which is equivalent to 50 mg of sitagliptin free base anhydrate;
    b) 500 mg of metformin hydrochloride;
    c) 48.2 mg of polyvinylpyrrolidone;
    d) 3.45 mg of sodium lauryl sulfate;
    e) 59.3 mg of microcrystalline cellulose;
    f) 13.8 mg of sodium stearyl fumarate; and
    g) 17.2 mg of a film coating.

23. A pharmaceutical composition in the form of a tablet comprising:
    a) 64.25 mg[*] of sitagliptin phosphate monohydrate, which is equivalent to 50 mg of sitagliptin free base anhydrate;
    b) 850 mg of metformin hydrochloride;
    c) 78.2 mg of polyvinylpyrrolidone;
    d) 5.60 mg of sodium lauryl sulfate;
    e) 96.1 mg of microcrystalline cellulose;
    f) 22.3 mg of sodium stearyl fumarate; and
    g) 27.9 mg of a film coating.

24. A pharmaceutical composition in the form of a tablet comprising:
    a) 64.25 mg[*] of sitagliptin phosphate monohydrate, which is equivalent to 50 mg of sitagliptin free base anhydrate;
    b) 1000 mg of metformin hydrochloride;
    c) 91.0 mg of polyvinylpyrrolidone;
    d) 6.50 mg of sodium lauryl sulfate;
    e) 112.3 mg of microcrystalline cellulose;
    f) 26 mg of sodium stearyl fumarate; and
    g) 32.5 mg of a film coating.

25. A pharmaceutical composition in the form of a tablet comprising:
    a) 64.25 mg[*] of sitagliptin phosphate monohydrate, which is equivalent to 50 mg of sitagliptin free base anhydrate;
    b) 500 mg of metformin hydrochloride;
    c) 48.2 mg of polyvinylpyrrolidone;
    d) 69.6 mg of microcrystalline cellulose;
    e) 6.89 mg of magnesium stearate; and
    f) 17.2 mg of a film coating.

26. A pharmaceutical composition in the form of a tablet comprising:
    a) 64.25 mg[*] of sitagliptin phosphate monohydrate, which is equivalent to 50 mg of sitagliptin free base anhydrate;
    b) 1000 mg of metformin hydrochloride;
    c) 91.0 mg of polyvinylpyrrolidone;
    d) 125.25 mg of microcrystalline cellulose;
    e) 13.0 mg of magnesium stearate;

f) 6.5 mg of sodium lauryl sulfate; and
g) 32.5 mg of a film coating.

27. A pharmaceutical composition in the form of a tablet comprising:
 a) 128.5 mg[*] of sitagliptin phosphate monohydrate, which is equivalent to 100 mg of sitagliptin free base anhydrite;
 b) 1000 mg of metformin hydrochloride;
 c) 91.0 mg of polyvinylpyrrolidone;
 d) 6.50 mg of sodium lauryl sulfate;
 e) 48 mg of microcrystalline cellulose; and
 f) 26 mg of sodium stearyl fumarate.

28. A pharmaceutical composition in the form of a tablet comprising:
 a) 128.5 mg[*] of sitagliptin phosphate monohydrate, which is equivalent to 100 mg of sitagliptin free base anhydrate;
 b) 500 mg of metformin hydrochloride;
 c) 53.8 mg of polyvinylpyrrolidone;
 d) 3.84 mg of sodium lauryl sulfate;
 e) 66.5 mg of microcrystalline cellulose; and
 f) 15.4 mg of sodium stearyl fumarate.

* * * * *

UNITED STATES PATENT AND TRADEMARK OFFICE
CERTIFICATE OF CORRECTION

PATENT NO. : 8,414,921 B2
APPLICATION NO. : 12/085722
DATED : April 9, 2013
INVENTOR(S) : Ashkan Kamali et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 587 days.

Signed and Sealed this
Ninth Day of July, 2013

Teresa Stanek Rea
*Acting Director of the United States Patent and Trademark Office*